United States Patent [19]

Flowers

[11] Patent Number: 5,024,361
[45] Date of Patent: Jun. 18, 1991

[54] SUPPLY CADDY

[76] Inventor: Joyce D. Flowers, 6330 Beechwood St., Philadelphia, Pa. 19138

[21] Appl. No.: 376,129

[22] Filed: Jul. 6, 1989

[51] Int. Cl.$^5$ .............................................. A45F 5/00
[52] U.S. Cl. .................................... 224/223; 224/245; 224/901; 224/904; 383/39
[58] Field of Search ................ 224/203, 205, 219–223, 224/226–229, 231, 233, 235, 236, 240, 241, 242, 245, 253, 267, 901, 904; 383/38, 39, 40; 206/316.2, 443; 190/109, 110; 24/306, 442

[56] References Cited

U.S. PATENT DOCUMENTS

| | | |
|---|---|---|
| D. 118,418 | 1/1940 | Picken . |
| D. 257,596 | 12/1980 | Rosenbloom, III ................. D2/229 |
| 1,486,470 | 3/1924 | Welch ............................. 224/245 X |
| 1,568,826 | 1/1926 | Gallemore . |
| 1,675,072 | 6/1928 | Watermon . |
| 2,846,685 | 8/1953 | Ehrich ....................................... 2/51 |
| 3,131,399 | 5/1964 | Murphy et al. ........................... 2/48 |
| 4,079,767 | 3/1978 | Howard ........................... 224/901 X |
| 4,210,186 | 7/1980 | Belenson ........................... 206/316.2 |
| 4,212,377 | 7/1980 | Weinreb ........................... 190/110 X |
| 4,461,332 | 7/1984 | Parkhurst ......................... 224/901 X |
| 4,498,615 | 2/1985 | Johnson .......................... 224/901 X |
| 4,545,079 | 10/1985 | Bakken ..................................... 2/48 |
| 4,793,394 | 12/1988 | Cohen .............................. 224/901 X |
| 4,796,790 | 11/1989 | Hamilton ............................. 224/253 |
| 4,819,846 | 4/1989 | Hannemann ........................ 224/240 |
| 4,842,032 | 6/1989 | Mastronardo ............... 206/316.2 X |
| 4,848,624 | 7/1989 | Clem .................................... 224/222 |
| 4,880,315 | 11/1989 | Berry et al. ........................... 383/39 |

*Primary Examiner*—Henry J. Recla
*Assistant Examiner*—Robert M. Fetsuga
*Attorney, Agent, or Firm*—Volpe and Koenig

[57] ABSTRACT

A supply caddy having a main body portion defining a pocket which is selectively subdivided by vertical and horizontal strips which are repositionable within the pocket. The caddy may be attached to a wearer by a strap.

5 Claims, 1 Drawing Sheet

SUPPLY CADDY

BACKGROUND OF THE INVENTION

1. Field of the Invention

The present invention relates generally to caddies or aprons for use with tools or supplies, and is particularly intended for use by doctors, nurses, and medical technicians.

2. Description of the Prior Art

The use of caddies or aprons to hold tools within the reach of the wearer is generally known in various trades. Generally, these aprons are comprised of canvas or other similar cloth that is able to withstand wear and to support the weight of tools. The prior art devices sometimes included fixed pockets and/or tool hangers. However, the prior art devices did not permit adjustment of the pocket size and/or relocation of the hangers. None of the known prior articles have been devised especially for use in the medical profession. Prior to this time, instruments used in the medical profession were generally carried in the pockets of uniforms, jackets, or lab coats.

One of the problems encountered with the known art is the inability to quickly or easily locate instruments or tools because they do not have a specifically designated area of placement in the pouch. A second prior art problem is the inability to adjust the configuration of the pockets and/or placement of the tool hangers to fit the differing sizes and shapes of the tools.

One advantage of the invention is the adjustable pocket size.

Another advantage of the invention is the adjustability of the tool hanger location.

SUMMARY OF THE INVENTION

The present invention provides a means for locating and keeping tools and instruments readily available. The present invention provides a supply caddy having a main body portion which is united along three respective edges to define a large open pocket accessible along the upper horizontal edge. The pocket is selectively divided into at least two smaller pockets. Specially configured tool hangers may be secured to the body portion.

DETAILED DESCRIPTION OF THE INVENTION

In the preferred embodiment the main body portion 10 of the caddy is comprised of pile material, resembling terry cloth, having a plurality of loops, hereinafter referred to as loop pile material 30. The means for selectively subdividing the pocket are comprised of pile material having a plurality of hooks, hereinafter referred to as hook pile material 28, which mates with the loop pile material 30. One material having these characteristics is known under the trademark Velcro ®. Velcro ® materials are well known as means for adjustable fastening. Each of the materials has a different face surface which mates with the opposite face surface to form a connection. The base surface or backing of each material is usually a smooth plane.

Figure 1:
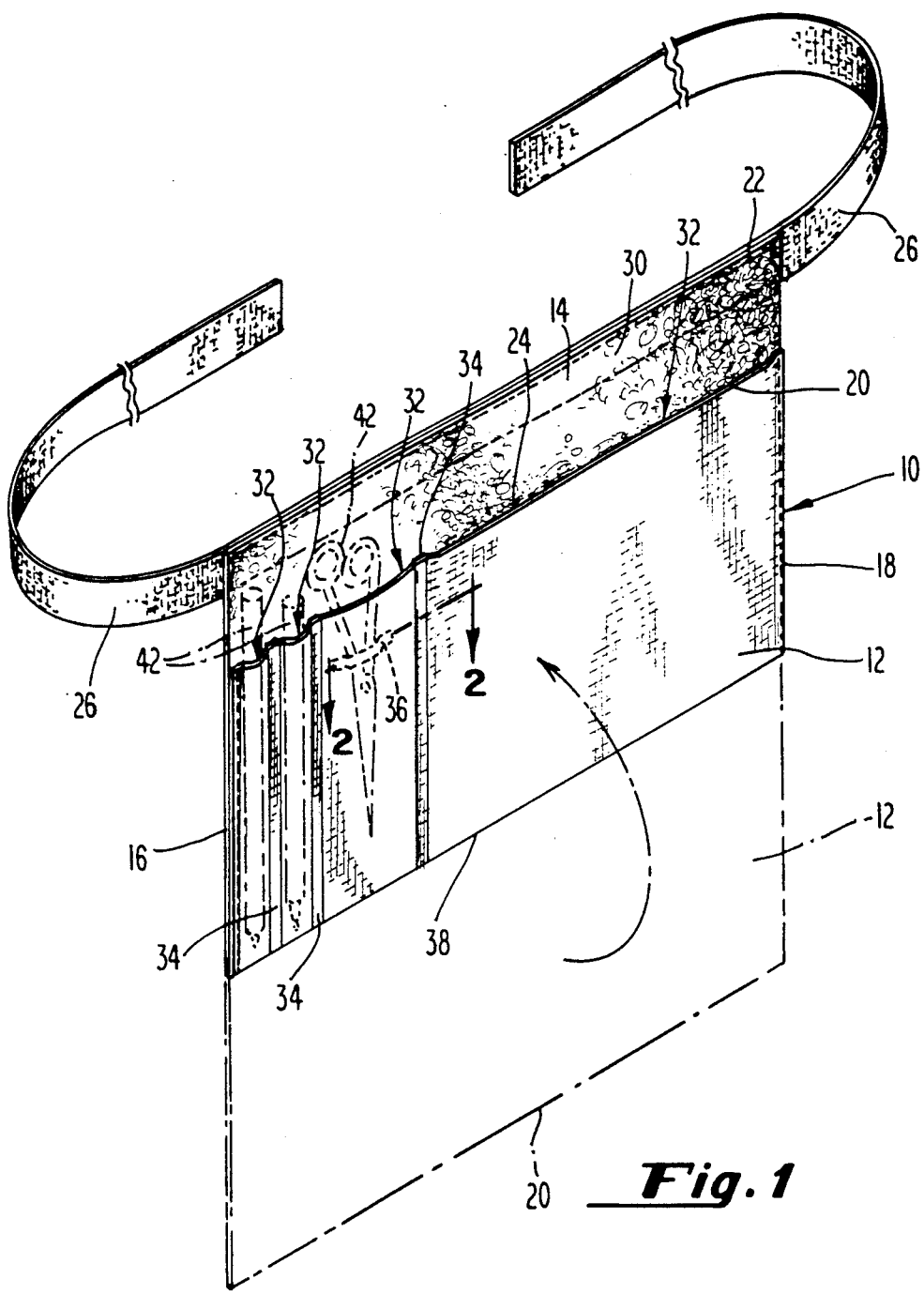
FIG. 1 is a perspective view of the supply caddy, illustrating plural pocket sections, a fragmented strap, instruments in phantom, and a part of the main body portion shown in phantom prior to stitching along the vertical edges according to the teachings of the present invention.

With reference to FIG. 1, there is shown a supply caddy in accordance with the present invention. The main body portion 10 is, preferably, comprised of a rectangularly-shaped continuous piece of material. The material is folded, approximately in half to yield front and back portions 12 and 14, and is united along vertical edges 16 and 18. The front horizontal edge 20 of the main body portion 10 is preferably located below the rear horizontal edge 22 of the main body portion for ease of access as shown in FIG. 1. If desired, the horizontal edges 20 and 22 may coincide.

In the preferred embodiment, the vertical edges 16 and 18 are united, preferably by stitching, to form at least one long pocket 24 across the width of the body portion 10. Alternatively, the edges 16 and 18 of the inner wall of the main body portion 10, if comprised of loop pile material 30, may be closed or attached by double-faced hook pile material 28 to render the present invention completely adjustable.

Figure 2:
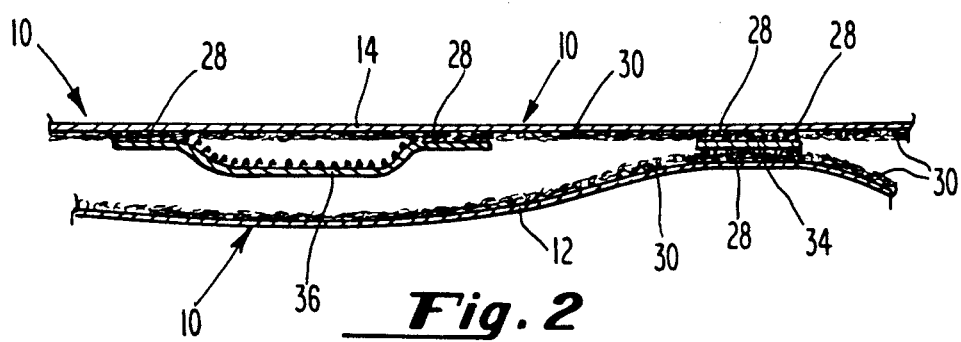
FIG. 2 is a cross-sectional view of the supply caddy along line 2—2 of FIG. 1, illustrating a double-faced strip and a single-faced strip.

Referring to FIG. 2, there is shown a cross-sectional view of a double-faced strip 34 and a single-faced strip 36 located within the wall of main body portion 10. As shown, the inner walls of the main body portion 10 are comprised of loop pile material 30. Double-faced strip 34 has hook pile material 28 on both surfaces or faces which is shown engaged with the loop pile material 30 of the respective portions 12 and 14. FIG. 2 also shows a single-faced strip 36 having hook pile material 28 on one surface or face selectively engaged with the loop pile material 30 of wall portion 14. Alternately, a portion of the hook pile material 28 may be removed from that portion of the strip 36 shown which is not engaged with the wall of the main body portion 10.

Referring again to FIG. 1, the pocket 24 is divided into four smaller pockets 32 by three double-faced strips 34 which, as shown in FIG. 2, have hook pile material 28 on both faces thereof. The width of these pockets 32 is selectively sized and adjusted by the placement of double-faced strip 34.

The smaller pockets 32 are further customized or tailored by a single-faced strip 36. The single-faced strip 36 when selectively placed may form a loop or tool hanger. As shown, the loop will hold an instrument, such as 42, securely and still allow for easy access to the instrument.

If desired, a double-faced strip, such as 34, may also be placed at any attitude with the main body portion 10 to define the depth of a pocket.

A strap 26 is secured along the rear horizontal edge 22 of the main body portion 10. The strap 26 may be made of any suitable material. Obviously, the strap 26 must be made of material having sufficient strength to withstand the weight of the instruments or tools 42 being carried within the caddy. The strap 26 may be tied around the waist area of a wearer. If comprised of complementary hook and pile material such as the known Velcro ® materials, the strap 26 may be easily placed around and removed from the waist area of a wearer.

Alternatively, the caddy may be comprised of two separate rectangularly-shaped portions 12 and 14 united along vertical edges 16, 18 and along a horizontal edge 38 to form the pocket 24. Preferably the front and back portions 12, 14 include the loop pile material 30.

Alternately, the front portion 12 may be comprised of hook pile material 28 and the back portion 14 may be comprised of loop pile material 30. In this embodiment there is no need for double-faced strips 34 or single-faced strips 36 because the front and back portions 12 and 14 mate with each other. With this embodiment, caution must be exercised to keep the front and back portions 12 and 14 from being pushed completely together which may render the caddy difficult to open.

I claim:

1. A supply caddy comprising:

a rectangularly-shaped continuous piece of material which is folded and defines a pocket, at least a portion of the inner walls of the pocket being comprised of loop pile material;

at least one double-faced strip which mates with the inner walls of the pocket, with at least a portion of hook pile material on both faces, and is repositionable within the pocket; and, at least one single-faced strip which mates with the inner wall of the pocket, with at least a portion of hook pile material on the one face, and is repositionable within the pocket to further subdivide it.

2. The caddy of claim 1, wherein the inner walls of the pocket are loop pile material.

3. The caddy of claim 1, wherein the double-faced strip is hook pile material.

4. The caddy of claim 1, wherein the single-faced strip is hook pile material.

5. The caddy of claim 1, wherein the caddy includes means for attachment to a wearer.

* * * * *